(12) United States Patent
Kawashima et al.

(10) Patent No.: US 7,306,613 B2
(45) Date of Patent: Dec. 11, 2007

(54) ENDOSCOPIC INSTRUMENTS

(75) Inventors: Koichi Kawashima, Hachioji (JP); Takayuki Suzuki, Yokohama (JP); Yoshio Onuki, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 493 days.

(21) Appl. No.: 10/114,127

(22) Filed: Apr. 3, 2002

(65) Prior Publication Data

US 2003/0004544 A1     Jan. 2, 2003

Related U.S. Application Data

(60) Provisional application No. 60/281,015, filed on Apr. 4, 2001.

(51) Int. Cl.
*A61B 17/04*     (2006.01)

(52) U.S. Cl. .................. 606/148; 606/224; 600/104

(58) Field of Classification Search ............ 606/1, 606/138–150, 181–183, 185–189, 222–233, 606/167, 170; 604/19, 22, 272, 164.01, 264, 604/523, 909; 600/101, 104, 85
See application file for complete search history.

(56) References Cited

U.S. PATENT DOCUMENTS

| | | | |
|---|---|---|---|
| 3,643,653 A | | 2/1972 | Takahashi et al. |
| 4,493,323 A | * | 1/1985 | Albright et al. ............ 606/144 |
| 5,037,021 A | | 8/1991 | Mills et al. |
| 5,397,326 A | | 3/1995 | Mangum |
| 5,474,543 A | * | 12/1995 | McKay ...................... 604/272 |
| 5,741,277 A | | 4/1998 | Gordon et al. |
| 5,792,153 A | | 8/1998 | Swain et al. |
| 5,797,927 A | | 8/1998 | Yoon |
| 5,814,065 A | * | 9/1998 | Diaz .......................... 606/213 |
| 5,860,992 A | | 1/1999 | Daniel et al. |
| 5,887,594 A | | 3/1999 | LoCicero, III |
| 5,895,395 A | * | 4/1999 | Yeung ........................ 606/144 |
| 5,897,507 A | * | 4/1999 | Kortenbach et al. ........ 600/562 |
| 5,984,932 A | | 11/1999 | Yoon |
| 5,993,466 A | | 11/1999 | Yoon |
| 6,071,233 A | * | 6/2000 | Ishikawa et al. ............ 600/104 |
| 6,113,609 A | | 9/2000 | Adams |

(Continued)

FOREIGN PATENT DOCUMENTS

EP     1284120     *     4/2002     ............... 600/101

(Continued)

*Primary Examiner*—Glenn K. Dawson
(74) *Attorney, Agent, or Firm*—Frishauf, Holtz, Goodman & Chick, P.C.

(57) ABSTRACT

A tissue-piercing device includes two piercing members, and an operation section to which a proximal end of each of the piercing members is connected. Each of the piercing members includes a flexible outer sheath, a slidable inner sheath which is slidably inserted in the outer sheath, and a slidable needle which is inserted in the inner sheath. A switch portion is provided for switching between an operation mode in which a piercing action by the two piercing members is performed in a single operation, and an operation mode in which piercing actions by the two piercing members are performed in respective separate operations. The switch portion includes a sheath-coupling member to couple and decouple the two slidable inner sheaths. The switch portion may include a needle-coupling member to couple and decouple the two slidable needles.

9 Claims, 12 Drawing Sheets

U.S. PATENT DOCUMENTS

| | | |
|---|---|---|
| 6,179,776 B1 | 1/2001 | Adams et al. |
| 6,352,503 B1 | 3/2002 | Matsui et al. |
| 6,409,678 B1 | 6/2002 | Ouchi |
| 6,494,888 B1 | 12/2002 | Laufer et al. |
| 6,551,315 B2 * | 4/2003 | Kortenbach et al. ........... 606/46 |
| 6,605,096 B1 * | 8/2003 | Ritchart ...................... 606/144 |
| 6,663,639 B1 | 12/2003 | Laufer et al. |
| 2002/0111534 A1 * | 8/2002 | Suzuki et al. ............... 600/102 |
| 2002/0156344 A1 | 10/2002 | Pasricha et al. |
| 2003/0004544 A1 | 1/2003 | Kawashima |
| 2003/0171651 A1 | 9/2003 | Page et al. |
| 2003/0199731 A1 | 10/2003 | Silverman et al. |
| 2003/0216753 A1 | 11/2003 | Nishtala et al. |
| 2005/0245945 A1 * | 11/2005 | Ewers et al. ................. 606/153 |

FOREIGN PATENT DOCUMENTS

| | | | | |
|---|---|---|---|---|
| JP | 2000-033071 A | | 2/2000 | |
| JP | 2000-037348 A | | 2/2000 | |
| JP | 2000-157552 | * | 6/2000 | ................. 600/101 |
| WO | WO 99/22649 | | 5/1999 | |

* cited by examiner

ENDOSCOPIC INSTRUMENTS

CROSS-REFERENCE TO RELATED APPLICATION

This application claims the benefit of U.S. Provisional Application to Koichi Kawashima et al, entitled "Endoscopic Instruments," application No. 60/281,015, filed Apr. 4, 2001.

BACKGROUND OF THE INVENTION

1. Field of the Invention

The present invention relates to suture instruments that are used for endoscopically suturing tissue in the living body, especially to those suture instruments used in conjunction with flexible endoscopes.

2. Description of the Related Art

Currently, in many cases, in-vivo tissue of a patient is sutured through surgical operation. A surgical operation, however, is highly invasive because it naturally requires an incision to the patient body. Furthermore, it requires post-operative hospitalization, the cost of which can be a heavy burden for the patient. In these circumstances, the development of a low-invasive oral endoscopic procedure that eliminates the need for open surgery is anticipated.

For example, there is an instrument for suturing in-vivo tissue through an oral endoscopic, the arrangement of which has been disclosed in the U.S. Pat. No. 5,792,153. (See FIG. 22 through FIG. 26)

The instrument (a) which can be mounted on an endoscope, comprises a tube (b) that can be connected to the suction source, a cavity (c) to which the tube (b) is joined, a hollow needle (d) inserted in the forceps channel of the endoscope, a tag (g) provided with a lumen and side holes (e and f) that can be incorporated into the needle, a wire (i) with a valve (h) which can move back and forth in the needle (d) and can be mounted to the side hole (e) detachably, a thread (j) tied to the tag (g), and a grasping member (k) which is provided at the tip of the cavity (c) and is easily connected and disconnected to the side hole (f).

With the valve (h) joined to the side hole (e), the tag (g) is inserted into the needle (d). Then, an endoscope, with the instrument (a) mounted on it, is orally inserted into the patient lumen to suck the tissue (l) to be sutured into the cavity (c). The tissue (l) is then penetrated with the needle (d) that has been thrust out through the endoscope tip. Next, the wire (i) is pushed forward to thrust out the tag (g) through the needle (d) so that the side hole (f) of the tag (g) can be joined to the grasping member (k). The valve (h) is then removed from the side hole (e) so as to pull the wire (i) and the needle (d) into the endoscope. After this, suction is released.

Again, the tissue (l) is sucked into the cavity (c) to be penetrated with the needle (d). Then the valve (h) is joined to the side hole (e) and the grasping member (k) is removed from the opening (f). The valve (h), the tag (g) and the needle (d) are withdrawn and the suction is released. The steps above are repeated as many times as are necessary and then the instrument (a) is removed from the lumen together with the endoscope. When both ends of the thread, which have been pulled out from the body, are tied together and fixed, the suture procedure is terminated.

However, in the arrangement disclosed in U.S. Pat. No. 5,792,153, fine control of location of the penetration is very difficult because penetration is performed with the tissue placed inside the cavity. This will prevent the tissue from being securely sutured, or will require more stitches than necessary, resulting in extended operation time.

Moreover, inability to control the intervals between the stitches will prevent the tissue from being securely sutured with less number of stitches.

In addition, each penetration requires joining the valve (h) and the side hole (e) and releasing the grasping member (k) and the opening (f) and vice versa. These two operations, required per penetration, will make the treatment procedure very complicated, extending the treatment time as well.

Application of the procedure will be limited because the size of the cavity determines the area to penetrate at one time, making suture impossible when the suture area is too large to suck in the cavity. If the length or the height of the cavity is increased to hold more tissue to be sutured, there will inevitably be an increase in length and diameter of the instrument (a) itself, making it impossible to insert it into the body lumen or to locate the penetration for accurate suture. These can not only impose more burdens onto the patient at the time of its insertion but also possibly extend the treatment time.

The instrument (a) requires inserting the tag (g) into the needle (d) from the tip of the needle. This can accidentally cause the operator to prick his finger with the needle while he is trying to insert the tag into it.

SUMMARY OF THE INVENTION

The first objective of the present invention is to provide a suture instrument that can accurately suture in-vivo tissue.

The second objective of the present invention is to provide a suture instrument that enables easy access to the suture area and delicate control of the location of the penetration needle.

The third objective of the present invention is to provide a suture instrument that enables easy operation and ensures a short treatment time.

The fourth objective of the present invention is to provide a suture instrument imposing no limitation to the suture area of the in-vivo tissue.

The fifth objective of the present invention is to provide a suture instrument that enables easy insertion into the body lumen with minimum harm to the patient.

The sixth objective of the present invention is to provide a suture instrument that ensures a higher level of safety for both operator and patient.

In accordance with the present invention, a tissue-piercing device to be used with an endoscope has two piercing members and each piercing member has a needle. The two needles may be parallel and apart from each other.

In addition, the two needles may be hollow.

The tissue-piercing device may also include operation sections at the proximal ends of the piercing members; a distal coupling member for connecting distal ends of the piercing members; and a proximal coupling member for connecting the operation sections of the piercing members.

The distal coupling member may be formed to be mounted to the distal end of the endoscope, and the proximal coupling member may be formed to be mounted to the operation section of the endoscope. Furthermore, the distal coupling member may be a cap and the cap may be made of transparent material.

Each piercing member may include a flexible outer sheath, a slidable flexible inner sheath which is inserted in the outer sheath and is extended from or retracted into the distal end of the outer sheath, a slidable needle which is inserted in the inner sheath and is extended from or retracted into the distal end of the inner sheath, a housing to be connected to the proximal end of the outer sheath, an inner sheath operation means connected to the proximal end of the inner sheath for moving back and forth the inner sheath, and a needle operation means connected to the proximal end of the needle for moving back and forth the needle.

The tissue-piercing device may also include a switch means for switching between a two-piercing member operation and a separate operation. It may also include a switch means for switching between a two-needle/inner sheath operation and a separate operation. When the switch means selects a two-needle operation, the needle extension may be varied to allow piercing the tissue with one needle after another The endoscope may be a flexible endoscope. The tissue-piercing device may be used to suture tissue in the human body.

Figure 21:
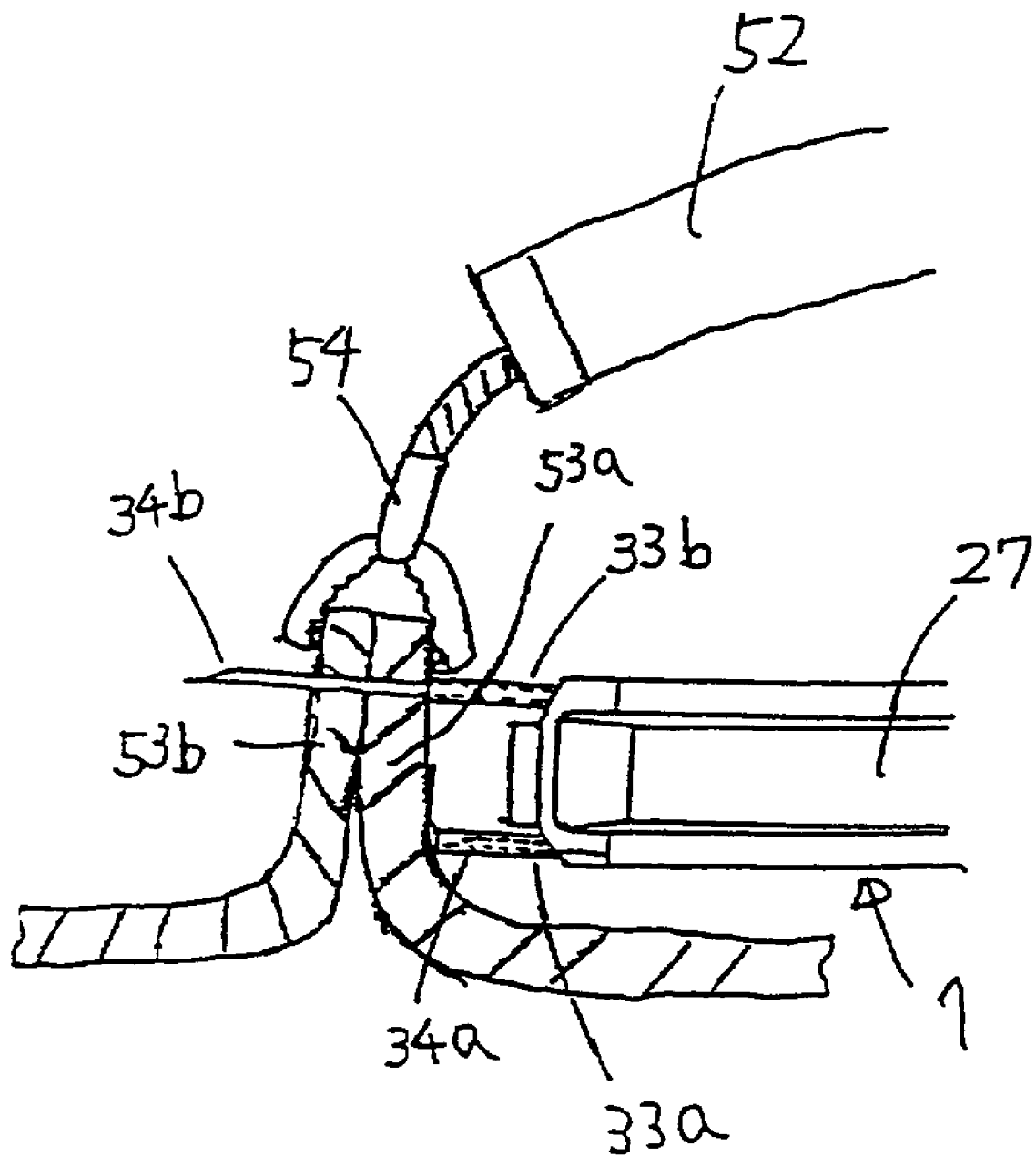
Figure 22:
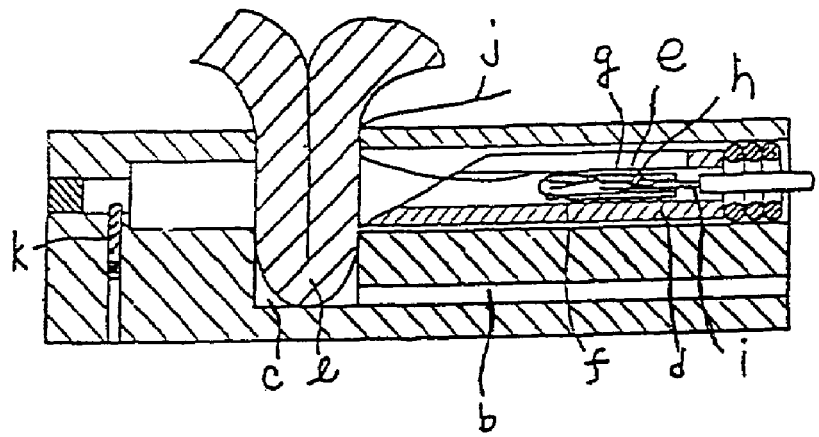
Figure 23:
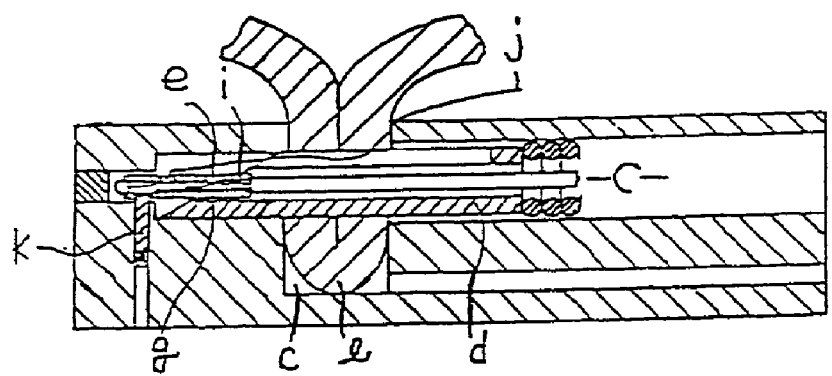
Figure 24:
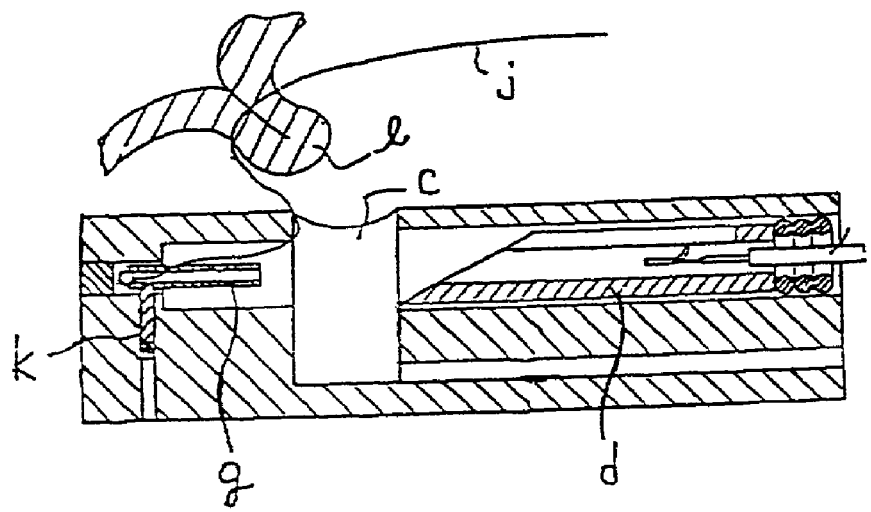
Figure 25:
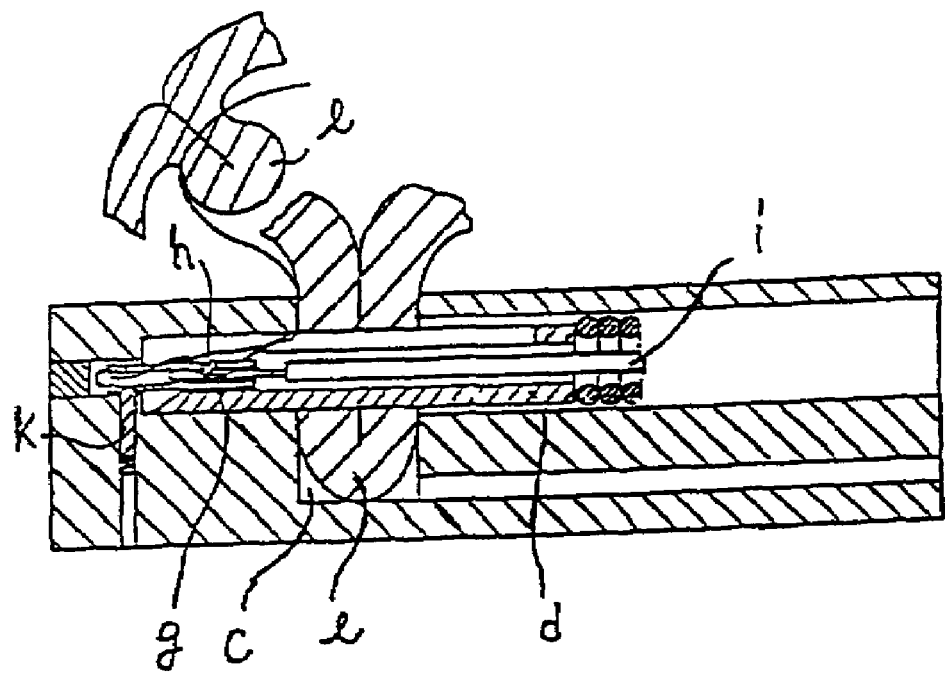
Figure 26:
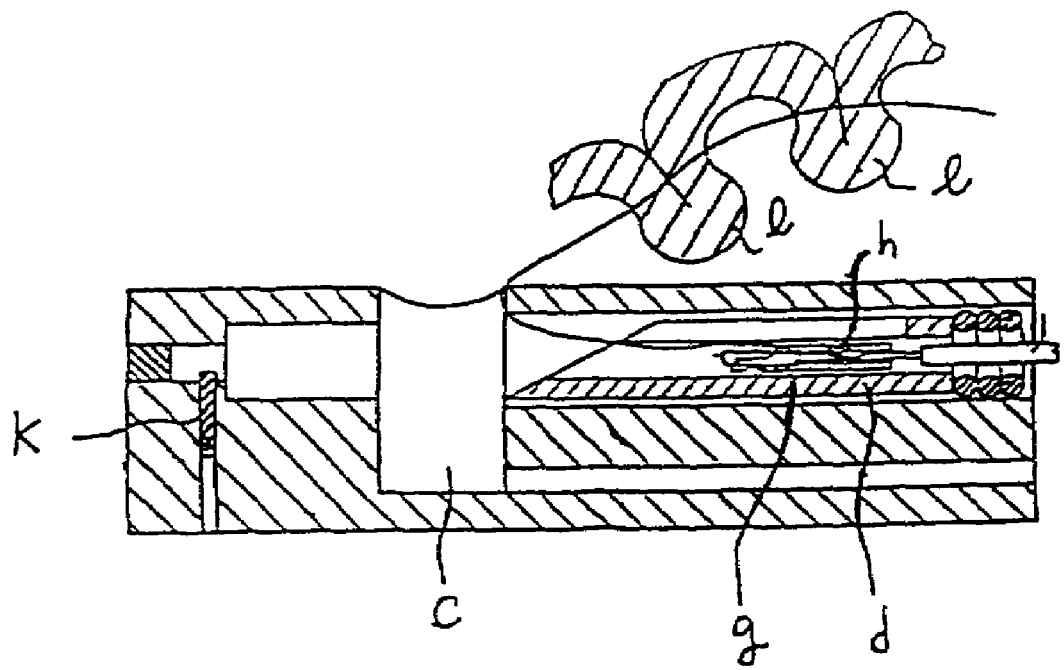

FIG. 21 shows piercing tissue using the piercing device according to the second embodiment; and FIGS. 22-26 show a suturing instrument according to U.S. Pat. No. 5,792,153.

DESCRIPTION OF THE PREFERRED EMBODIMENTS

First Embodiment (FIGS. 1 to 18)

Description of a Piercing Device and a Knot Pusher (FIGS. 1 to 9)

A piercing device 1 comprises a main body 2, inner sheaths 3a and 3b, needles 4 and 13, an inner sheaths-coupling member 5, and a needles-coupling member 6.

The main body 2 comprises two outer sheaths 7a and 7b, caps 8 connected at the distal ends of the sheaths 7a and 7b, and an operation section 9 connected at the proximal end of the sheaths 7a and 7b. The cap 8 comprises an outer sheaths-connecting section 10, a distal cylindrical section 11, and a distal mounting section 12. The distal cylindrical section 11 is made of a relatively hard material. Preferably, it is made of a transparent plastic material such as polycarbonate lest it should obstruct the vision of a first endoscope 27. Preferably, the inner diameter is about 5 to 15 mm, the wall thickness is about 1 mm. The length is about 3 to 10 mm, and a shorter cylinder is better.

The distal mounting section 12 is cylindrical and is inserted detachably to the distal end of the first endoscope 27. The first endoscope is flexible endoscope. The distal mounting section 12 is made of a relatively soft plastic material such as PVC or other thermoplastic elastomer. Its inner diameter depends on the size of the distal end of the endoscope to be used and is generally about 10 mm. The outer sheaths-connecting section 10 has a ring section fixed over the periphery of the distal cylindrical section 11, and connection legs 14a and 14b which are extending longitudinally and axially, parallel with each other. The connection legs 14a and 14b are preferably positioned at opposite sides and 180 degrees apart from one another. The connection legs 14a and 14b are preferably apart by 10 to 20 mm, depending on the outer diameter of the distal cylindrical section 11. The connection legs 14a and 14b have penetration holes and form openings 15a and 15b at the distal end.

The outer sheaths 7a and 7b are hollow and flexible enough to follow the curvature of the first endoscope 27.

For example, they are plastic tubes made of fluoroplastics, polyethylene, polyamide, polyimide, polyurethane or other thermoplastic elastomer, or metal coils. They may be metal coils covered by plastic tubes. They may be plastic tubes with metal mesh to prevent kink. The inner diameter is about 1 to 2 mm, the outer diameter is about 1.5 to 3 mm, and the length is about 1 to 1.5 m. The distal ends of the outer sheaths 7a and 7b are fixed to the connection legs 14a and 14b and are in parallel positions. The openings 15a and 15b are connected and communicated with the lumen of the outer sheaths 7a and 7b.

The operation section 9 comprises a base 16, grips 17a and 17b, sliders (inner sheath operation means) 18a and 18b, a proximal mounting section 20, and a channel port 21. The proximal ends of the outer sheaths 7a and 7b penetrate the base 16 and are connected to the distal ends of the grips 17a and 17b.

The grips 17a and 17b are cylindrical, and have screws 24a and 24b on the periphery of the proximal ends with which slider locks 22a and 22b are engaged. Between the screws 24a and 24b and the slider locks 22a and 22b, there are elastic tubular fixing rings 23a and 23b made of rubber such as silicon rubber or fluorine rubber, or thermoplastic elastomer. Sliders 18a and 18b are positioned slidably inside the fixing rings 23a and 23b. When the slider locks 22a and 22b are tightened, the fixing rings 23a and 23b are pressed longitudinally and expanded radially to immobilize the sliders 18a and 18b.

The sliders 18a and 18b are cylindrical. They are comprised of slider stoppers 25a and 25b at the proximal end for limiting a sliding area against the grips 17a and 17b, slider port 19a and 19b, and narrow sections 26a and 26b for connecting the inner sheaths-coupling member 5. The proximal mounting section 20 is mounted at the distal end of the base 16, and is fixed detachably to a forceps channel port 28 of the first endoscope 27.

The channel port 21 is mounted to the proximal end of the base 16, and is plugged detachably with a forceps valve 29. The channel port 21 is connected through the lumen of the proximal mounting section 20 and the lumen in the base 16 to the forceps channel (not shown) of the first endoscope 27.

The inner sheath 3a or 3b comprises an inner sheath port 30, an inner sheath pipe 31, an O ring 32, and a sheath section 33. The inner sheath 3a or 3b can be inserted via the slider port 19 into the outer sheath 7.

When the inner sheath 3 is inserted to the outer sheath 7, the inner sheath port 30 is connected detachably to the slider port 19. The inner sheath port 30 has a lumen.

The inner sheath pipe 31 is connected to the sheath section 33 and the inner sheath port 30. The lumen of the inner sheath pipe 31 is also communicated with the lumen of the sheath section 33 and the lumen of the inner sheath port 30.

The O ring 32 is held between the proximal end of the inner sheath pipe 31 and the inner sheath port 30. It is made of elastic rubber such as silicon rubber or fluororubber, or thermoplastic elastomer. It is received in grooves 51a and 51b of needle bodies 34a and 34b of the needles 4 and 13, which is described later, and stops movement of the needle bodies 34a and 34b.

The sheath section 33 is hollow and flexible enough to follow the curvature of the first endoscope 27. For example, it is a plastic tube made of fluoroplastics, polyethylene, polyamide, polyimide, polyurethane or other thermoplastic elastomer, or a metal coil. It may be a plastic tube with metal mesh to prevent kink. The inner diameter is about 0.5 to 1.5 mm, and the outer diameter is about 1 to 2.5 mm.

When the slider 18 slides against the grip 17, The sheath section 33 slides in the outer sheath 7. The length of the inner sheath 3 is adjusted so that the distal end of the sheath section 33 is positioned proximal to the opening 15 when the slider 18 is pulled completely from the grip 17, and the distal end of the sheath section 33 is positioned distally about 15 to 50 mm from the opening 15 of the cap 8 when the slider 18 is pushed sufficiently to touch the grip 17.

The needle 4 comprises the needle body 34a, a needle grip (needle operation means) 35 connected to the proximal end of the needle body 34a, and suture-holding forceps 38 inserted in them.

The needle 13 comprises the needle body 34b, a needle grip (needle operation means) 46 connected to the proximal end of the needle body 34b, and a suture 47 inserted movably in the needle body 34b and the needle grip 46.

The needle 4 or 13 can be inserted through the inner sheath port 30 into the inner sheaths 3a or 3b.

The needle bodies 34a and 34b are a metal pipe made of stainless steel or nitinol, which is resistant to pressure from the proximal end during piercing and flexible enough to follow the curvature of the first endoscope 27. The inner diameter is about 0.5 mm and the outer diameter is about 1 mm. To facilitate projection of the distal end of the needle bodies 34a and 34b out of the distal end of the inner sheaths 3a and 3b, the outer diameter of the needle bodies 34a and 34b preferably approximates the inner diameter of the inner sheaths 3a and 3b. The needle bodies 34a and 34b have two grooves 51a and 51b near the proximal end.

The needle bodies 34a and 34b slides in the inner sheaths 3a and 3b by needle grip 35 and 46 moving back and forth against the inner sheath port 30a and 30b. When the O ring 32 of the inner sheath 3 is engaged in the groove 51a, the distal end of the needle body 34 is positioned slightly proximal than the distal end of the sheath section 33, and when the O ring 32 is engaged in the groove 51b, the distal end of the needle body 34 extends out of the distal end of the sheath section 33. Preferably, the needle body 34 extends out of the distal end of the sheath section 33 by about 50 to 70 mm. Preferably, the distal ends of the needle bodies 34a and 34b should be apart by at least 10 mm when the needle bodies 34a and 34b extend out of the distal ends of the sheath sections 33a and 33b.

The needle grip 35 comprises a port body 36, a needle port 37, and a elastic cylindrical fixing ring 42 between them made of rubber such as silicon rubber or fluororubber, or thermoplastic elastomer. The port body 36 is connected to the proximal end of the needle body 34a. The port body 36 and the needle port 37 have lumen and are connected with screws. An operation pipe 40 of the suture-holding forceps 38 slides in the lumen. When the needle port 37 is tightened, the fixing ring 42 is pressed longitudinally and expanded radially to fix the operation pipe 40. The needle port 37 has a narrow section 43 to which the needles-coupling member 6 is connected. The needle grip 46 also has a narrow section 43 to which the needles-coupling member 6 is connected.

The suture-holding forceps 38 are inserted in advance into the needle body 34a and the needle grip 35 for sliding.

The suture-holding forceps 38 has a holding section 41 at the distal end of the operation pipe 40. The holding section 41 is formed at least two hook shaped nail 50. The holding section 41 is bent and mounted to the operation pipe 40 so that the central axis 48 of the holding section 41 forming the holding section 41 inclines against the longitudinal axis of the operation pipe 40.

The length L of the holding section 41 is longer than the distance l between the two needle bodies 34a and 34b, and the suture end 49 of the suture 47 extending out of the needle 13 is inserted in the holding section 41.

The holding section 41 is a metal wire made of stainless steel or nitinol, or plastic wire. The wire may be a single wire or a stranded wire. It has the diameter that allows retracting the holding section 41 into the needle body 34a. The holding section 41 is adjusted to open by 10 to 20 mm when it extends out of the needle body 34a.

The operation pipe 40 extends from the proximal end of the holding section 41 to the proximal end of the needle port 37. The operation pipe 40 is connected an operation knob 39 at the proximal end. The operation pipe 40 is a slim metal pipe for smooth rotation such as stainless steel or nitinol. The holding section 41 is rotated following the rotation of the operation knob 39.

The suture 47 is a general surgical suture made of, for example, nylon or silk. The suture 47 is 0.2 to 0.5 mm thick, and preferably 0.3 to 0.4 mm thick.

The inner sheaths-coupling member 5 can be mounted to the narrow sections 26a and 26b of the sliders 18a and 18b detachably.

The inner sheaths-coupling member 5 is an elastic yet relatively hard plastic sheet. There are two slits 44a and 44b on one side, which are connected to coupling holes 45a and 45b.

The width of the slits 44a and 44b are slightly narrower than the outer diameter of the narrow sections 26a and 26b of the sliders 18a and 18b. The inner diameter of the coupling holes 45a and 45b is nearly equal to the outer diameter of the narrow sections 26a and 26b. The each distance between the slits 44a and 44b, or coupling holes 45a and 45b is equal to the distance between the narrow sections 26a and 26b. When the slits 44a and 44b are pressed to the narrow sections 26a and 26b, the slits 44a and 44b open to connect the coupling holes 45a and 45b with the narrow sections 26a and 26b.

To remove the inner sheaths-coupling member 5, the narrow sections 26a and 26b are pulled out of the slits 44a and 44b.

When the inner sheaths-coupling member 5 is mounted to the sliders 18a and 18b, both inner sheaths 3a and 3b can be moved back and forth at one time either by holding and moving one slider 18 or the inner sheaths-coupling member 5. The inner sheaths 3a and 3b extend by the same length out of the openings 15a and 15b.

To change the extension length of either inner sheath 3a or 3b, the inner sheaths-coupling member 5 is removed, and the sliders 18a and 18b are operated separately.

The needles-coupling member (switch means) 6 and the inner sheaths-coupling member (switch means) 5 are similarly composed and function as the switch means either singly or together. The needles-coupling member 6 can be detachably mounted to the narrow section 43a and 43b of the needle ports 37 and the needle grip 46. According to mounting and removing the needles-coupling member 6, the needles 4 and 13 are operated at one time or separately. When the separate operation is selected, the extension length of the needles 4 and 13 out of the distal end of the inner sheath 3a or 3b may be varied.

Figure 1:
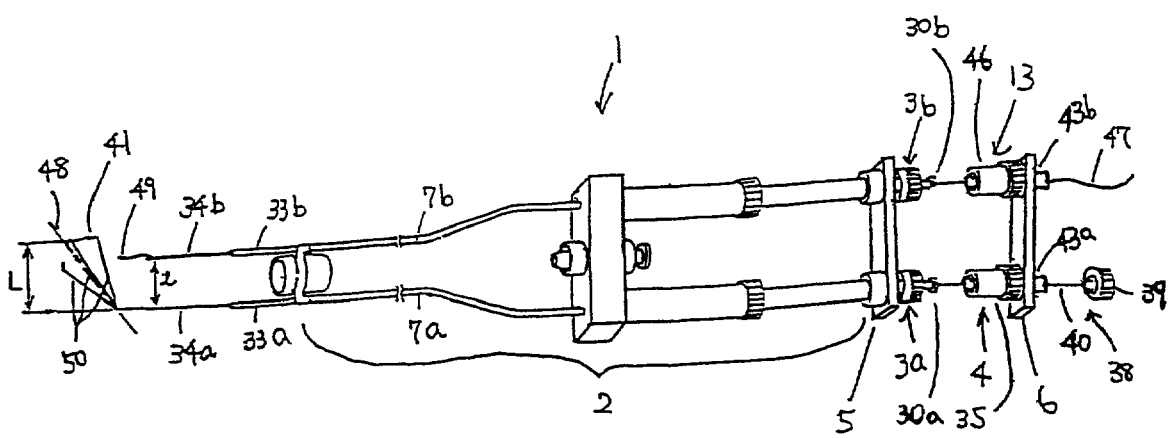
FIG. 1 shows a piercing device according to a first embodiment of the present invention.
Figure 2:
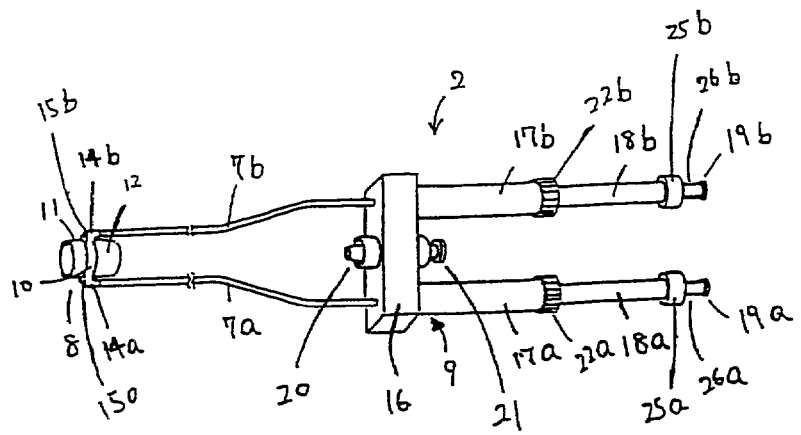
FIG. 2 shows a main body of the piercing device according to the first embodiment.
Figure 3:
FIG. 3 shows an inner sheath according to the present invention.
Figure 4:
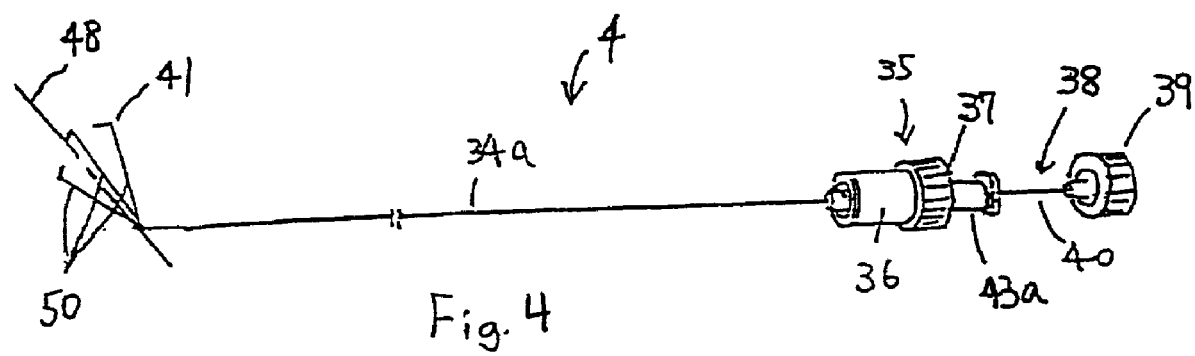
FIG. 4 shows a first needle according to the present invention.
Figure 5:
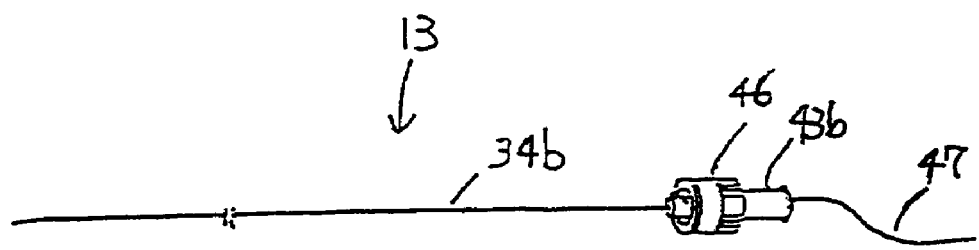
FIG. 5 shows a second needle according to the present invention.
Figure 6:
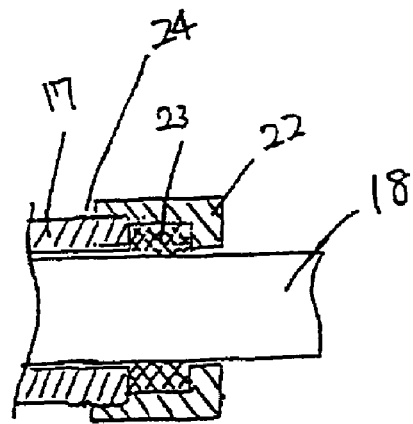
FIG. 6 is a cross-sectional view of a proximal end of a grip of the operation section of the piercing device according to the first embodiment.
Figure 7:
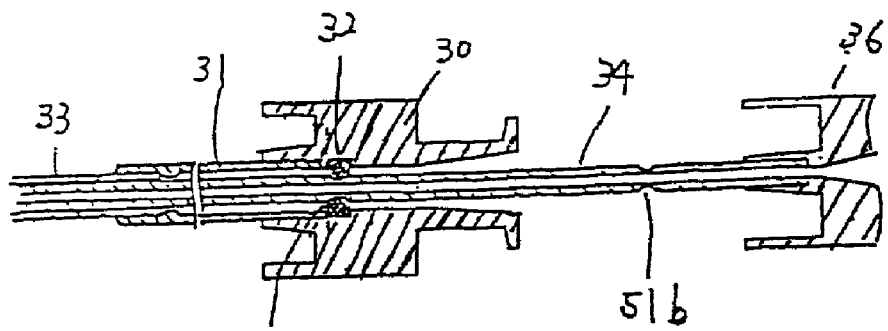
FIG. 7 is a cross-sectional view of the first needle inserted into the inner sheath.
Figure 8:
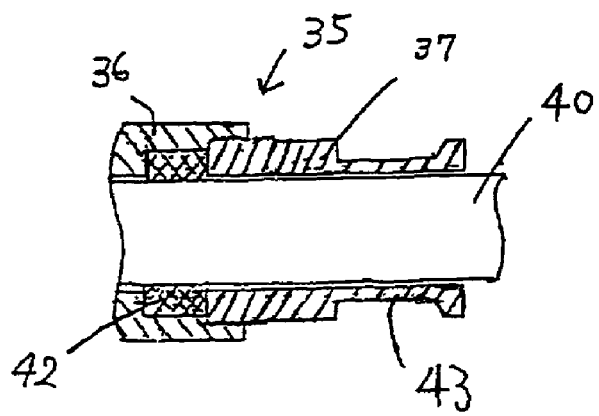
FIG. 8 is a cross sectional view of the needle grip of the first needle.
Figure 9:
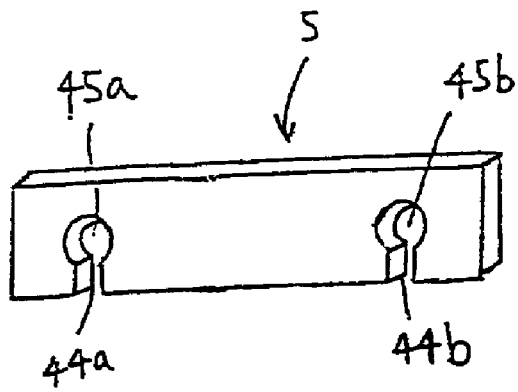
FIG. 9 shows a needles-coupling member according to the first embodiment.
Figure 10:
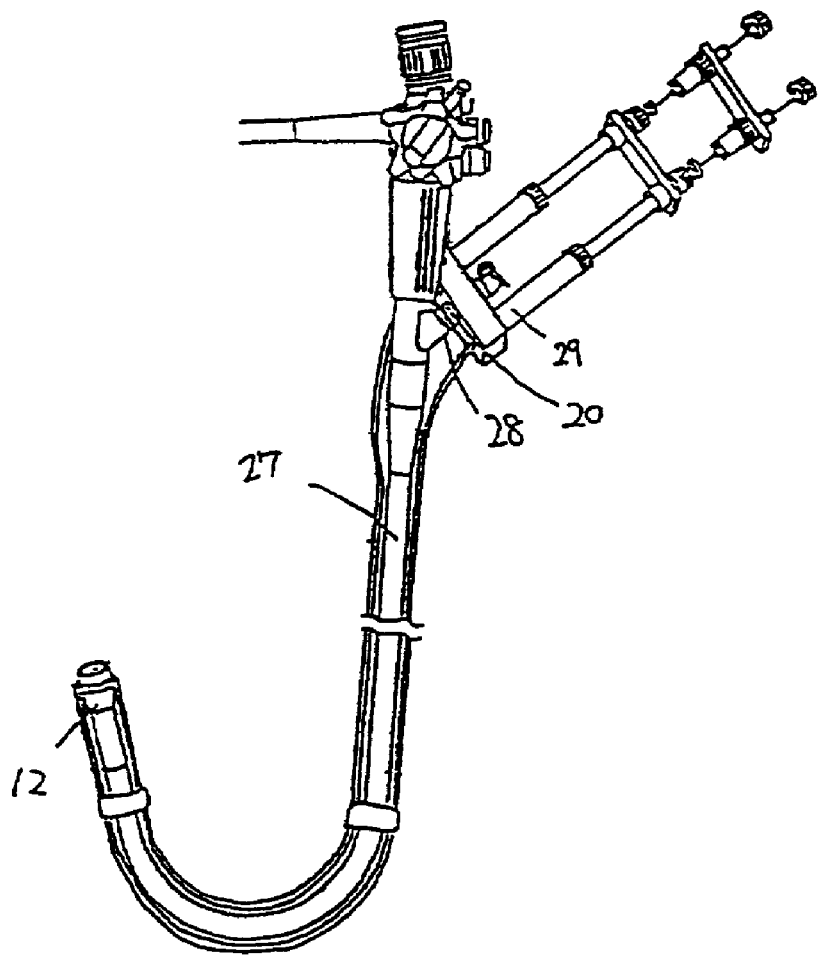
FIG. 10 shows the piercing device according to the first embodiment mounted to an endoscope.

Mounting the Device to an Endoscope (FIG. 10)

The piercing device 1 is mounted in the following procedure. The proximal mounting section 20 is mounted to the forceps channel port 28 of the first endoscope 27. The distal mounting section 12 of the cap 8 is inserted to the distal end of the first endoscope 27 while the outer sheaths 7a and 7b are held lest they should be twisted. The outer sheaths 7a and 7b are fixed at several points on the outer periphery of the first endoscope 27 with surgical tape.

The inner sheaths 3a and 3b are inserted through the slider ports 19a and 19b to the outer sheaths 7a and 7b, and the inner sheath port 30a and 30b are connected and fixed to the slider ports 19a and 19b. With the suture-holding forceps 38 placed completely into the needle bodies 34a, the needle 4 is inserted through the inner sheath port 30a into the inner sheaths 3a.

With the distal end of the suture 47 placed completely into the needle bodies 34b, the needle 13 is inserted through the inner sheath port 30b into the inner sheaths 3b. The groove 51a of the needle bodies 34a and 34b should be engaged with the O ring 32 of the inner sheaths 3a and 3b. The needle bodies 34a and 34b are then positioned so as not to extend out of the distal ends of the sheath sections 33a and 33b.

The sliders 18a and 18b are pulled proximally. The sheath sections 33a and 33b are pulled in the outer sheaths 7a and 7b in advance so that the distal ends of the sheath sections 33a and 33b are positioned more proximally than the openings 15a and 15b.

Figure 11:
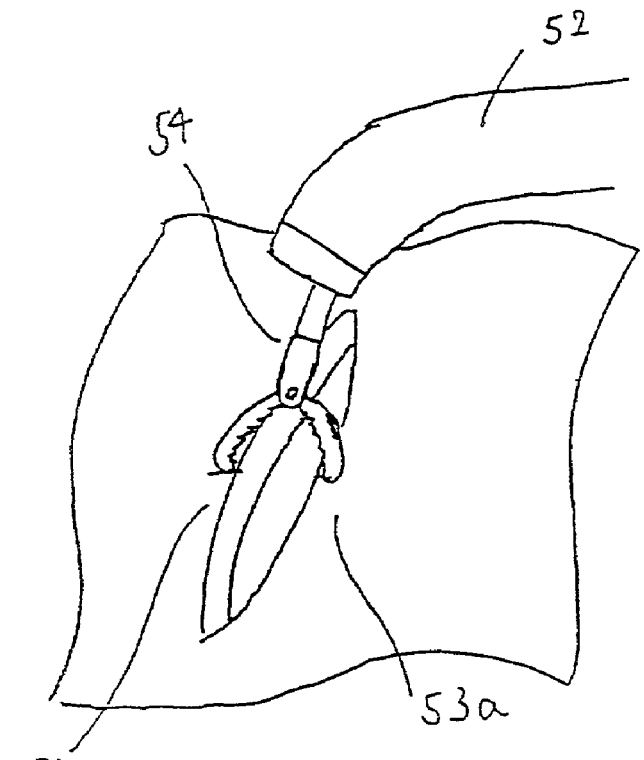
FIG. 11 shows grasping tissue using a second endoscope.
Figure 12:
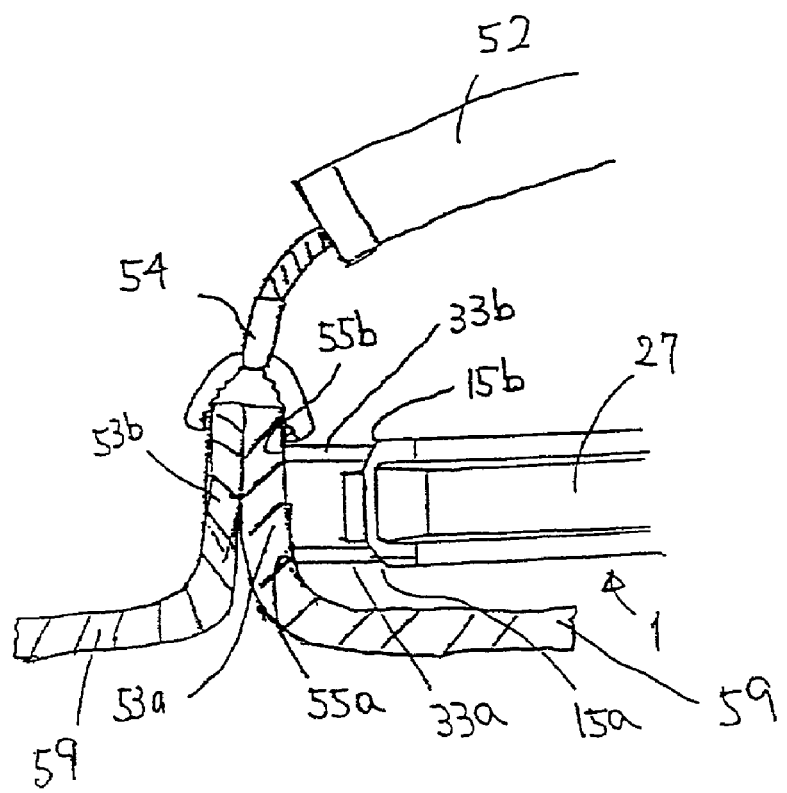
FIGS. 12 and 13 show piercing the tissue using the piercing device of the first embodiment.
Figure 13:
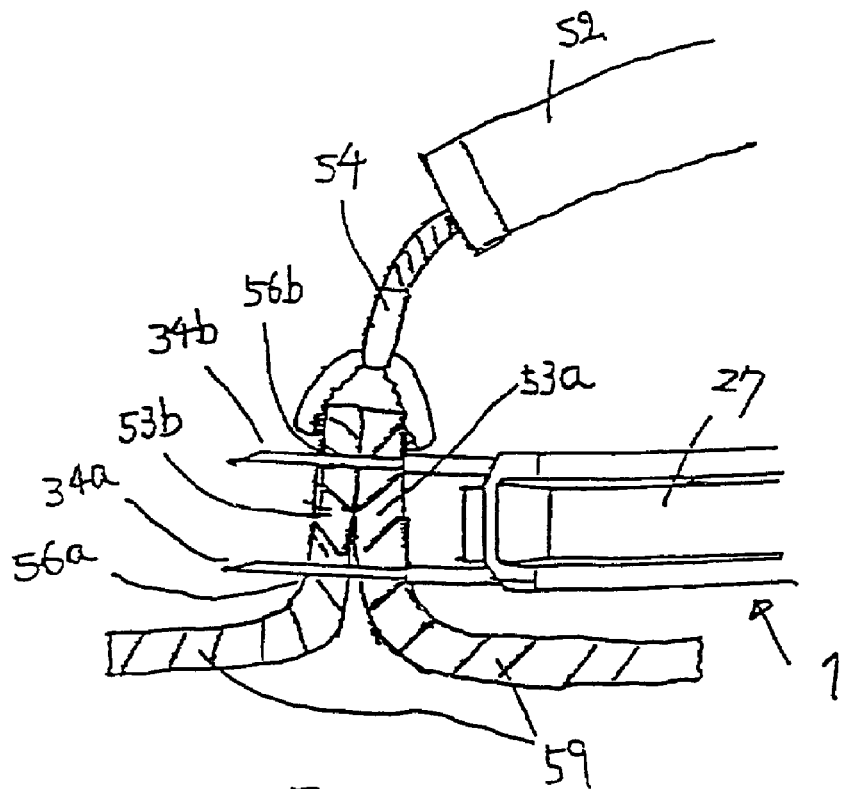

Pulling Up and Penetration the Suture Area (FIGS. 11 to 13)

The second endoscope 52 is inserted into the patient body. The distal end of the second endoscope 52 is positioned near sutured tissues 53a and 53b.

The sutured tissues 53a and 53b are grasped and pulled up together by a grasping forceps 54 which is inserted through a forceps channel (not shown) of the second endoscope 52. The grasping forceps 54 may be of any design and shape as long as it can grasp the sutured tissues 53a and 53b. Next, the first endoscope 27 mounted the piercing device 1 is inserted into the patient's body. The distal end of the first endoscope 27 is positioned near the sutured tissue 53a. The sliders 18a and 18b are moved against the grips 17a and 17b to the distal end. The sheath sections 33a and 33b are extended out of the openings 15a and 15b and pressed against the entering points 55a and 55b. Depending on the relative position between the sutured tissue 53a and the distal end of the first endoscope 27, the inner sheaths-coupling member 5 is either attached to the narrow sections 26a and 26b to press the sheath sections 33a and 33b at one time, or is removed to press the sheath sections 33a and 33b separately. After the sheaths sections 33a and 33b are pressed, the needle port 37 of the needle grip 35 is tightened to the port body 36 to fix the sliders 18a and 18b.

The needle grips 35 and 46 are pressed toward the distal end until the groove 51b of the needle bodies 34a and 34b is engaged with the O ring 32, and the needle bodies 34a and 34b are extended out of the sheath sections 33a and 33b.

The needles-coupling member 6 is either attached to the narrow sections 43a and 43b to press the needle bodies 34a and 34b at one time, or is removed to press the needle bodies 34a and 34b separately. Pressing the needle bodies 34a and 34b at one time makes operation easy, but increases penetration resistance of the needles and requires more force to penetrate them into tissue. On the other hand, pressing the needle bodies 34a and 34b separately makes it easy to penetrate the tissue, but requires two rounds of penetration procedures. When the needle bodies 34a and 34b are extended out of the sheath sections 33a and 33b, they pass through the entering points 55a and 55b of the sutured tissue 53a and the exiting points 56a and 56b of the sutured tissue 53b.

The second endoscope 52 is used to check that the needle bodies 34a and 34b project from the sutured tissue 53b. In the first embodiment two needle bodies 34a and 34b are penetrated through the sutured tissues 53a and 53b when the surface comprised with the needle bodies 34a and 34b locates tissue 59 vertically. The needle bodies 34a and 34b may be penetrated when the surface locates tissue 59 horizontally. In the case, suture area spreads horizontally.

Figure 14:
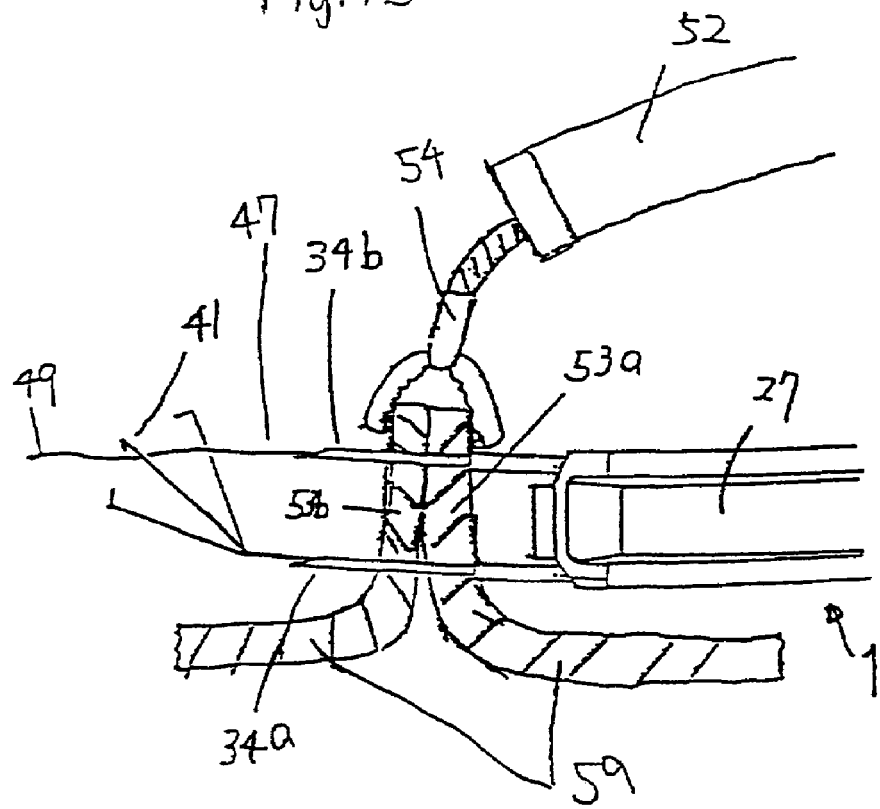
FIGS. 14-16 show the insertion of a suture into the tissue using the tissue-piercing member of the first embodiment.
Figure 15:
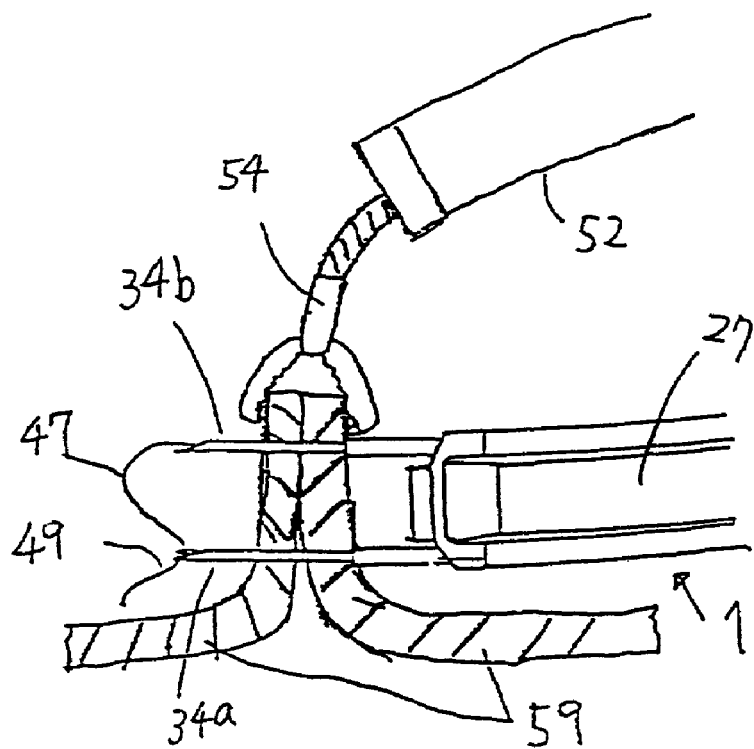
Figure 16:
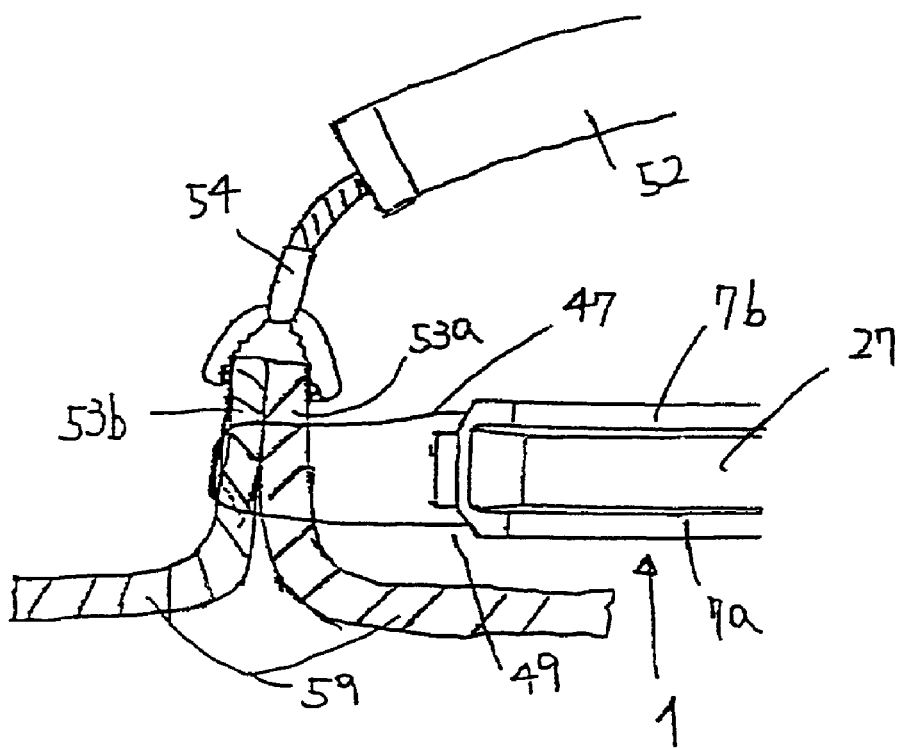

Inserting a Suture into Tissue (FIGS. 14 to 16)

The operation knob 39 of the needle 4 is pressed toward the distal end and the holding section 41 is extended out of the distal end of the needle body 34a while it is observed by the second endoscope 52. The operation knob 39 is rotated while it is observed by the second endoscope 52 to rotate the holding section 41 until the longitudinal axis of the needle body 34b is positioned in the holding section 41. The suture 47 in the needle 13 is pressed out, and the suture end 49 is inserted in the holding section 41.

The operation knob 39 is pulled proximally to pull the holding section 41 into the needle body 34a and hold the suture end 49. The needle port 37 of the needle grip 35 is tightened to the port body 36 to lock the holding section 41 and the suture end 49.

Next, with the suture 47 extending from the proximal end of the needle grip 46 released, the needle grips 35 and 46 are pulled back proximally to retract the distal ends of the needle bodies 34a and 34b into the sheath sections 33a and 33b. Thus, the suture end 49 penetrates the sutured tissues 53a and 53b.

The slide locks 22a and 22b are loosened, and the grips 18a and 18b are pulled back proximally to pull the distal ends of the sheath sections 33a and 33b in the outer sheaths 7a and 7b. With the suture 47 extending from the proximal end of the needle grip 46 released, the first endoscope 27 and piercing device is then removed from the patient body. The needle port 37 of the needle grip 35 is loosened to port body 36, and the operation knob 39 is pressed toward the distal end to remove the suture ends 49 out of the holding sections 41.

Next, with the suture end 49 held, the first endoscope 25 mounted piercing device 1 is pulled back proximally to pull out another suture end 57 of the suture 47 from the distal end of the needle body 34b. After the sutured tissues 53a and 53b is released from the grasping forceps 54, the grasping forceps 54 and second endoscope 52 is removed from the patient body.

Figure 17:
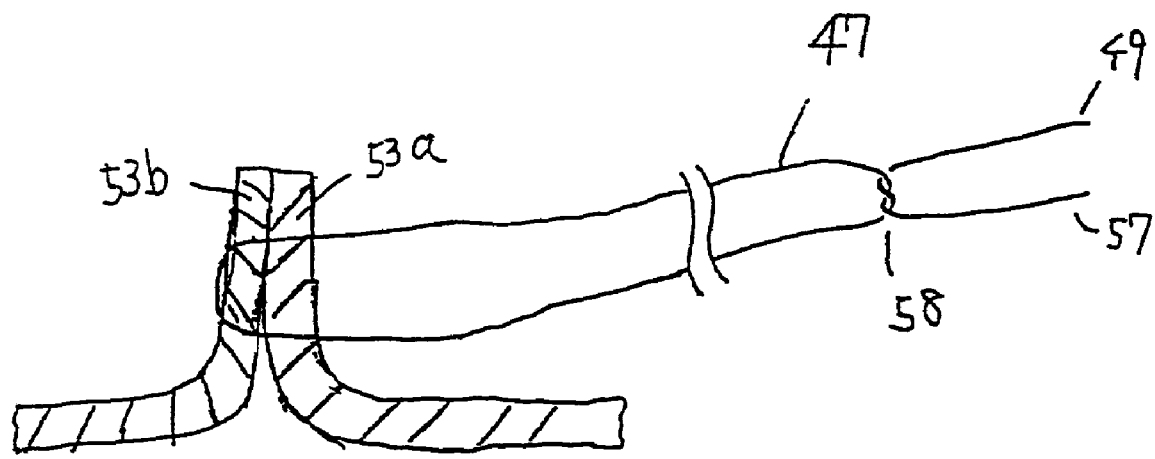
FIGS. 17 and 18 show fixing the suture.
Figure 18:
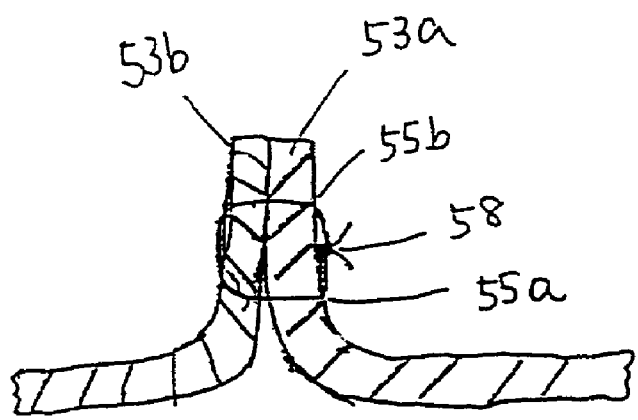

Fixing the Suture (FIGS. 17 and 18)

The suture ends 49 and 57 are tied outside the patient body to form a knot 58. The knot 58 can be any knot as long as it is generally used in surgical operation. The knot 58 is advanced into the patient body by a general knot pusher introduced through a forceps channel of the first endoscope 27 of the second endoscope 52 while it is observed by the either endoscope.

When the knot 58 reaches near the entering points 55a and 55b of the sutured tissue 53a, the knot pusher is pressed against the sutured tissue 53a, while the suture ends 49 and 57 are pulled to lock the knot 58.

The above procedure is repeated several times before it is checked that the knot 58 is tied firmly. Then the endoscope and the knot pusher are removed from the patient body.

Finally, excess sutures beyond the knot 58 are cut using endoscopic scissors, and are collected outside the body. Depending on length and area of the sutured tissue 53a and 53b, the above procedure is repeated to suture the sutured tissue 53a and 53b completely.

The piercing device 1 is so designed that the sheath sections 33a and 33b touch the targeted penetration point before the needle bodies 34a and 34b are actually thrust into the tissue. This provides easy location of the penetration point before penetration is actually performed with the needles, as well as delicate control of the location. As a result, an accurate suture, an easy operation for the treatment, and a great reduction in treatment time are implemented.

Integrated beforehand into the piercing device 1 are two penetration needles. Therefore, once the distal end of the endoscope 27 approaches the point of penetration on the sutured tissue 53a, the two needles are ready for immediate penetration. This feature also contributes to easy operation and great reduction in treatment time.

The piercing device 1 is equipped with two penetration needles located in parallel to each other at a fixed interval beforehand. This allows the sutured tissues 53a and 53b to be sutured at a fixed interval when a number of stitches are made, ensuring the suture accuracy.

The outer sheaths 7a and 7b that the needles 4a and 4b are inserted through are mounted onto the cap 8 beforehand at a given point. Therefore, once the cap 8 is mounted on the distal end of the endoscope 27, both outer sheaths 7a and 7b can be readily mounted at a location given against the distal end of the endoscope 27. This also contributes to reduction in the time required for mounting it onto the endoscope.

Penetration with the needle bodies 34a and 34b is performed on the sutured tissues 53a and 53b while they are grasped and pulled up with the grasping forceps 54 inserted through the second endoscope 52. Thus the penetration area and therefore the suture area are to be selected at will.

The penetration area can be extended when the sutured tissues 53a and 53b are further pulled up. As a means of pulling up the sutured tissues 53a and 53b, the grasping forceps 54, independent of the piercing device 1, are used. This contributes to considerable miniaturization of the piercing device 1 itself, providing easy insertion into the body lumen of the patient, and reducing the pain caused to the patient when the piercing device 1 is inserted into the body lumen.

Since the need for inserting a suture thread or other material from the distal end of the needle bodies 34a and 34b is eliminated, there will be no danger of the operator being accidentally pricked with a needle.

Figure 19:
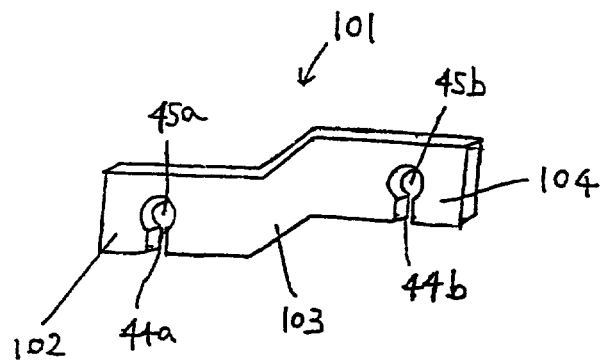
FIG. 19 shows a needles-coupling member according to a second embodiment of the present invention.
Figure 20:
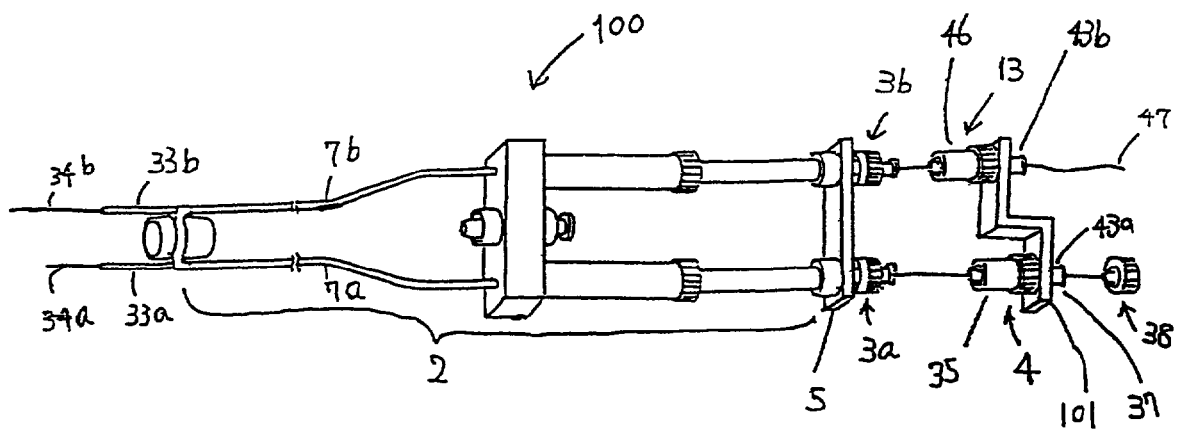
FIG. 20 shows a piercing device according to the second embodiment.

Second Embodiment (FIGS. 19 to 21)

Only points different from those of the first embodiment are described.

A piercing device 100 is the piercing device 1 with the needles-coupling member 6 replaced by a needles-coupling member 101. The needles-coupling member 101 comprising a distal section 102, a middle section 103 and a proximal section 104, and is shaped like a crank. The distal section 102 and the proximal section 104 are positioned longitudinally apart each other. The distal section 102 should be apart from the proximal section 104 by at least the thickness of tissue to be penetrated, or at least 5 mm.

Coupling holes 45a and 45b of the needles-coupling member 101 are mounted via the slits 44a and 44b to the narrow sections 43a and 43b of the needle port 37 and needle grip 46. Because the distal section 102 and the proximal section 104 are apart each other, the distal ends of the needle bodies 34a and 34b are longitudinally apart from each other. When the needles-coupling member 101 is held and pressed toward the distal end, the needle bodies 34a and 34b are extended out of the inner sheaths 33a and 33b with its distance between the two maintained.

When the piercing device 100 is used for penetrating the sutured tissues 53a and 53b, first needle body 34b penetrates the sutured tissues 53a and 53b; next needle body 34a penetrates them.

Because two needles never penetrates tissue at one time even if the needles coupling-member 101 is pressed to operate the two needles, penetration resistance will not be increased, and penetration is easy.

In the arrangement described above, the following operational advantages are gained.

The piercing device provides easy location of the penetration point before penetration is actually performed with the needles, as well as delicate control of the location. As a result, accurate suture, easy operation for treatment, and great reduction in treatment time are implemented.

Integrated into the piercing device are two penetration needles beforehand. Therefore, once the distal end of the endoscope approaches the targeted point of penetration on the tissue, the two needles are ready for immediate penetration. This feature also contributes to easy operation and great reduction in treatment time.

The piercing device is equipped with two penetration needles located in parallel to each other at a fixed interval beforehand. This allows the tissues to be sutured at a fixed interval when a number of stitches are made, ensuring the suture accuracy.

The two penetration needles are mounted beforehand at a given point on the cap that is provided at the distal end of the piercing device. Therefore, once the cap is mounted on the distal end of the endoscope, both two needles are readily mounted at a location given against the distal end of the endoscope. This also contributes to reduction in time required for mounting the device onto the endoscope.

Since the need for inserting a suture thread or other material from the distal end of the needle into the needle is eliminated, there will be no danger of the operator being accidentally pricked with a needle.

Penetration is performed on the in-vivo tissues while they are grasped and pulled up with the grasping forceps independent of the piercing device. Thus the penetration area and, therefore, the suture area are to be selected at will. The penetration area can be extended when the tissues are further pulled up. As a means of pulling up the tissues, the grasping forceps independent of the piercing device are used. This contributes to considerable miniaturization of the piercing device itself, providing easy insertion into the body lumen of the patient, and reducing the pain subject to the patient when the piercing device is inserted into the body lumen.

What is claimed is:

1. A tissue-piercing device for use with an endoscope for suturing or ligating tissues in body cavities, said tissue-piercing device comprising:
    two piercing members;
    an operation section to which a proximal end of each of the piercing members is connected; and
    a switch portion for switching between: (i) an operation mode in which a piercing action by said two piercing members is performed in a single operation, and (ii) an operation mode in which piercing actions by said two piercing members are performed in respective separate operations;
    wherein each of the piercing members comprises:
        a flexible outer sheath;
        a slidable inner sheath which is slidably inserted in the outer sheath to be extendable and retractable with respect to a distal end of the outer sheath;
        a slidable needle which is inserted in the inner sheath to be extendable and retractable with respect to a distal end portion of the inner sheath; and
    wherein the switch portion comprises a sheath-coupling member to couple and decouple the two slidable inner sheaths.

2. A tissue-piercing device according to claim 1, further comprising:
    a distal coupling member that connects the two piercing members;
    wherein a distal end portion of each of the piercing members is coupled to the distal coupling member such that the piercing members are substantially parallel and spaced apart at a substantially constant interval even when the tissue-piercing device is not mounted to the endoscope.

3. A tissue-piercing device according to claim 2, wherein said needles are hollow.

4. A tissue-piercing device according to claim 2, wherein the distal coupling member is mountable to a distal end of the endoscope.

5. A tissue-piercing device according to claim 2, wherein the distal coupling member comprises:
    a ring; and
    two connection members connected to the ring;
    wherein the two piercing members are respectively coupled to the two connection members.

6. A tissue-piercing device according to claim 5, wherein the ring is mounted to a distal connection cylinder, and the distal connection cylinder is mountable to a distal end of the endoscope.

7. A tissue-piercing device according to claim 1,
    wherein each of the piercing members further comprises:
        a housing which is connectable to a proximal end of the outer sheath;
        an inner sheath operation portion which is connected to a proximal end of the inner sheath and which is operable to move the inner sheath back and forth; and
        a needle operation portion which is connected to a proximal end of the needle and which is operable to move the needle back and forth; and
    wherein the two needles are arranged in parallel and spaced apart at a substantially constant interval.

8. A tissue-piercing device according to claim 7, wherein said needles are hollow.

9. A tissue-piercing device for use with an endoscope for suturing or ligating tissues in body cavities, said tissue-piercing device comprising:
    two piercing members;
    an operation section to which a proximal end of each of the piercing members is connected; and
    a switch portion for switching between: (i) an operation mode in which a piercing action by said two piercing members is performed in a single operation, and (ii) an operation mode in which piercing actions by said two piercing members are performed in respective separate operations;
    wherein each of the piercing members comprises:
        a flexible outer sheath;
        a slidable inner sheath which is slidably inserted in the outer sheath to be extendable and retractable with respect to a distal end of the outer sheath;
        a slidable needle which is inserted in the inner sheath to be extendable and retractable with respect to a distal end portion of the inner sheath;
    wherein the switch portion comprises a needle-coupling member to couple and decouple the two slidable needles; and
    wherein the switch portion further comprises a sheath-coupling member to couple and decouple the two slidable inner sheaths.

* * * * *